United States Patent [19]

Hampton

[11] Patent Number: 4,925,635
[45] Date of Patent: May 15, 1990

[54] TEMPERATURE CONTROL FOR A KOH TREATER

[75] Inventor: Joe B. Hampton, Bartlesville, Okla.

[73] Assignee: Phillips Petroleum Company, Bartlesville, Okla.

[21] Appl. No.: 261,810

[22] Filed: Oct. 24, 1988

Related U.S. Application Data

[62] Division of Ser. No. 714,226, Mar. 21, 1985, Pat. No. 4,797,199.

[51] Int. Cl.⁵ .................. G05D 9/00; G05D 23/00; F28D 7/00
[52] U.S. Cl. ........................... 422/202; 422/200; 422/201; 422/203; 422/106; 422/109; 422/111
[58] Field of Search .............. 422/173, 177, 202, 201, 422/203, 200, 105, 106, 108–112; 208/262.1, DIG. 1; 585/854, 712, 956, 723; 423/240 R, 240 S, DIG. 6

[56] References Cited

U.S. PATENT DOCUMENTS

| | | | |
|---|---|---|---|
| 3,471,582 | 10/1969 | Lupfer | 260/277 |
| 4,123,351 | 6/1979 | Chapman | 208/262 |
| 4,162,273 | 7/1979 | Skraba | 585/854 |
| 4,167,531 | 9/1979 | Potts | 585/854 |
| 4,224,283 | 9/1980 | Potts | 422/111 |
| 4,230,666 | 10/1980 | Chapman | 422/106 |
| 4,236,219 | 11/1980 | Killebrew | 364/501 |
| 4,797,199 | 1/1989 | Hampton | 208/262.1 |

Primary Examiner—H. M. S. Sneed
Assistant Examiner—Chung K. Pak
Attorney, Agent, or Firm—George E. Bogatie

[57] ABSTRACT

A cooling fluid is utilized to withdraw heat from a KOH treater. The passing of the cooling fluid in heat exchange with the KOH treater is controlled so as to maintain desired operating pressures for the cooling fluid and also to substantially maximize heat transfer. Bypassing of the feed around the KOH treater to prevent temperature runaway is utilized only if sufficient cooling cannot be provided by the cooling fluid to prevent temperature runaway.

5 Claims, 1 Drawing Sheet

TEMPERATURE CONTROL FOR A KOH TREATER

This application is a division of application Ser. No. 714,226 filed Mar. 21, 1985, now U.S. Pat. No. 4,797,199.

This invention relates to the control of temperature in a treater containing solid potassium hydroxide (KOH) utilized to remove hydrofluoric (HF) acid from propane in an HF alkylation process.

A conventional HF alkylation process is illustrated in U.S. Pat. No. 4,123,351. In such a process, propane is often present in the fresh isobutane feed, in the propylene feed and also some propane may be produced in the process. In order to prevent a build up of propane in the HF alkylation process, a depropanizer is commonly used to remove propane. Propane removed as an overhead from the depropanizer will generally contain some HF acid as well as other impurities. These impurities in some of the HF acid are generally removed in a stripping operation. However, even after stripping, some HF acid will remain and this remaining HF acid, which will be very small in concentration, is typically removed by contacting the propane stream containing a small or trace amount of HF acid with a bed of solid KOH. Substantially all of the HF acid will be removed from the propane by such contacting.

Upsets may occur in an HF alkylation process. Such upsets may cause an increase in the concentration of HF acid in the propane stream provided to the KOH treater. When too much HF acid contacts the KOH, the temperature starts to rise in the bed area due to the heat of reaction between KOH and HF acid. If excess HF acid is allowed to continue to flow to the KOH treater, high temperature excursions are experienced which can cause hydrocarbons charged to the KOH treater to vaporize and explosions may result. It is extremely desirable to avoid such temperature runaways and the resulting consequences.

In the past, temperature runaways have generally been prevented by bypassing the propane containing HF acid around the KOH treater if a temperature runaway is detected. However, while this procedure does prevent temperature runaways, it also results in a contamination of the propane withdrawn from the HF alkylation process or recycle is required.

It is thus an object of this invention to provide an improved method and apparatus for preventing temperature runaways in a KOH treater so as to substantially minimize the occasions on which bypassing of the feed around the KOH treater is required.

In accordance with the present invention, method and apparatus is provided whereby a cooling fluid (preferably isobutane) is passed in heat exchange with the KOH treater. Preferably, the cooling fluid is not only passed around the KOH bed treater but is also passed through standpipes in the KOH treater to maximize heat transfer. The passing of the cooling fluid in heat exchange with the KOH bed treater is controlled so as to maintain desired operating pressures and also substantially maximize heat transfer. Bypassing is also provided if a temperature runaway begins to occur even with the cooling provided by the heat exchange.

Other objects and advantages of the invention will be apparent from the foregoing brief description of the invention and the claims as well as the detailed description of the drawing which is briefly described as follows:

Figure 1:
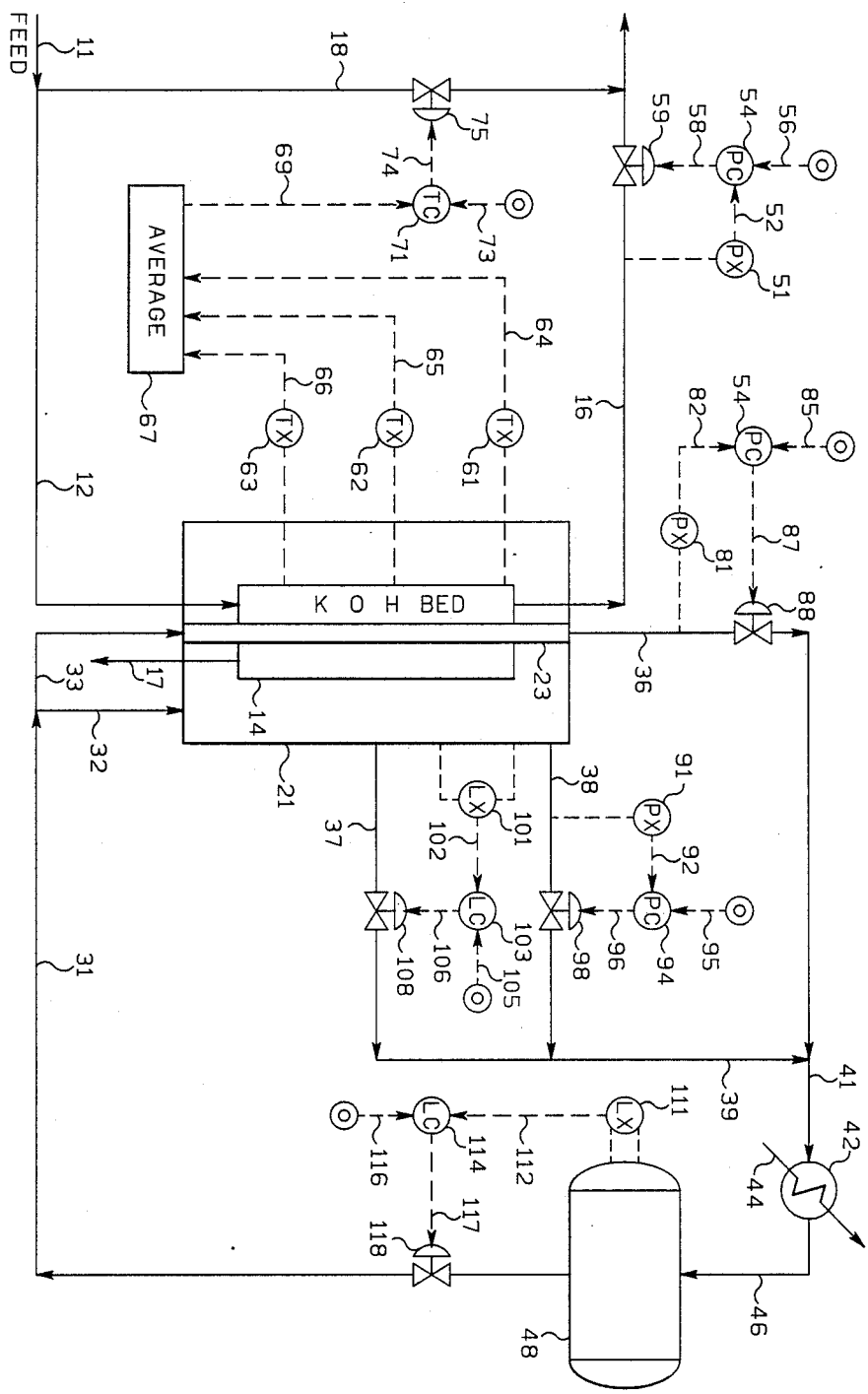
FIG. 1 is a diagrammatic illustration of a KOH treater, the associated cooling system of the present invention and also the associated control system of the present invention.

A specific control system configuration is set forth in FIG. 1 for the sake of illustration. However, the invention extends to different types of control system configurations which accomplish the purpose of the invention. Lines designated as signal lines in the drawings are electrical or pneumatic in this preferred embodiment. Transducing of these signals is not illustrated for the sake of simplicity because it is well known in the art that, if a variable is measured in pneumatic form, it must be transduced to electrical form if it is to be transmitted in electrical form by a transducer. Also, final signals to control valves may be pneumatic in form but the output from controllers will generally be electrical in form.

The invention is also applicable to mechanical, hydraulic or other signal means for transmitting information. In almost all control systems some combination of electrical, pneumatic, mechanical or hydraulic signals will be used. However, use of any other type of signal transmission, compatible with the process and equipment in use, is within the scope of the invention.

The controllers shown may utilize the various modes of control such as proportional, proportional-integral, proportional-derivative, or proportional-integral-derivative. In this preferred embodiment, proportional-integral-derivative controllers are utilized but any controller capable of accepting two input signals and producing a scaled output signal, representative of a comparison of the two input signals, is within the scope of the invention.

The scaling of an output signal by a controller is well known in control system art. Essentially, the output of a controller may be scaled to represent any desired factor or variable. An example of this is where a desired pressure and an actual pressure are compared by a controller. The output could be a signal representative of a desired change in the flow rate of some gas necessary to make the desired and actual pressures equal. On the other hand, the same output signal could be scaled to represent a percentage or could be scaled to represent a temperature change required to make the desired and actual pressures equal. If the controller output can range from 0 to 10 volts, which is typical, then the output signal could be scaled so that an output signal having a voltage level of 5.0 volts corresponds to 50 percent, some specified flow rate, or some specified temperature.

Referring now to FIG. 1, propane, which will generally contain only small amounts of HF acid (in the range of about 10 to about 50 ppm) is provided through the combination of conduits 11 and 12 to the KOH treater 14. The temperature of the feed flowing through conduit 11 will typically be about 100° F.

After passing in contact with the solid KOH (generally particulate or flaked in form) contained in the KOH treater 14, the propane flowing through conduit 12 is removed from the KOH treater 14 through conduit 16. The propane flowing through conduit 16 will contain substantially no HF acid.

A slurry of water, KOH and KOH-HF acid reaction product, which is generally referred to as slough, is removed from the KOH treater 14 through conduit 17. The feed flowing through conduit 11 may be bypassed around the KOH treater 14 through conduit 18.

The KOH treater 14 is surrounded by an external jacket 21. Also, a standpipe 23 extends through the KOH bed treater 14. If sufficient heat exchange can be achieved by using only the external jacket, then the standpipe extending through the KOH bed treater may not be required. Also, if desired, multiple standpipes could be extended through the KOH bed treater 14. Preferably, the standpipe 23 has fins which extend into the KOH bed treater so as to substantially maximize heat transfer.

While a particular heat exchange apparatus (external jacket and internal standpipes) is illustrated in FIG. 1 and is preferred, any suitable apparatus may be utilized for passing the cooling fluid, described hereinafter, in heat exchange with the KOH treater 14. The present invention is not limited to the use of any particular apparatus for such heat exchange.

A suitable cooling fluid is provided through the combination of conduits 31 and 32 to the external jacket. Also, the same cooling fluid is provided through the combination of conduits 31 and 33 to the internal standpipe 23. It is noted that the internal standpipe 23 and the external jacket 21 are preferably not in fluid communication.

Any suitable cooling fluid may be utilized. However, as previously stated, isobutane is a preferred cooling fluid. Isobutane is available in an HF alkylation plant and the use of isobutane avoids fouling which might occur if a cooling fluid such as water was utilized. Also, isobutane provides an excellent heat transfer from the KOH treater 14.

The isobutane flowing through the standpipe 23 is withdrawn through conduit 36. The isobutane in the external jacket 21 is withdrawn as a liquid through conduit 37 and as a vapor through conduit 38. Isobutane flowing through conduit 37 and 38 is combined and flows through conduit 39. Isobutane flowing through conduits 36 and 39 is combined and provided through conduit 41 to the heat exchanger 42.

A cooling fluid (preferably water) is provided to the heat exchanger 42 through conduit 44. The isobutane flowing through conduit 41 is cooled in the heat exchanger 42 and substantially condensed to a liquid form. The thus cooled isobutane is withdrawn from the heat exchanger 42 and is provided through conduit 46 to the accumulator 48. Liquid is withdrawn from the accumulator 48 and flows through conduit 31 as previously described.

Additional equipment such as pumps, additional heat exchangers and control components in addition to those which will be described hereinafter would typically be associated with the KOH treater 14 and the cooling system. However, these additional components have not been illustrated for the sake of simplicity since these additional components play no part in the description of the present invention.

The flow rate of the feed through conduits 11 and 12 is generally not controlled since this flow rate is controlled by upstream units. However, the flow of the propane through conduit 16 is controlled so as to maintain a desired pressure in the KOH treater 14.

Pressure transducer 51 in combination with a pressure sensing device, which is operably located in conduit 16, provides an output signal 52 which is representative of the actual pressure in conduit 16 and thus in the KOH treater 14. Signal 52 is provided as the process variable input to the pressure controller 54.

Pressure controller 54 is also provided with a set point signal 56 which is representative of the desired pressure of the propane exiting the KOH treater 14. This desired pressure is a pressure which will maintain the propane in liquid form at average operating temperatures in the KOH treater 14. Signal 56 will generally have a magnitude in the range of about 295 to about 360 psig.

In response to signals 52 and 56, the pressure controller 54 provides an output signal 58 which is responsive to the difference between signals 52 and 56. Signal 58 is scaled so as to be representative of the position of the control valve 59, which is operably located in conduit 16, required to maintain the actual pressure in the KOH treater 14 substantially equal to the desired pressure represented by signal 56. Signal 58 is provided from the pressure controller as a control signal for the control valve 59 and the control valve 59 is manipulated in response thereto.

It is noted that signal 58 may be considered as being representative of the desired flow rate of propane through conduit 16. In some cases signal 58 would be scaled so as to be representative of a desired flow rate and provided as a set point to a flow controller with the actual flow rate being provided as the process variable to the flow controller. The output of the flow controller would then be utilized to manipulate the control valve 59. Thus, whether signal 58 is scaled in such a manner that it can be provided directly to the control valve 59 or is scaled in such a manner that it can be provided directly as a set point to a flow controller, signal 58 is essentially being utilized to manipulate the flow rate and may be considered as being representative of a desired flow rate in either case.

As previously stated, a temperature runaway may occur under extreme conditions even with the cooling provided by the heat exchange previously described. Thus, as a safety precaution, temperature control is utilized to bypass at least a portion of the feed flowing through conduit 11 around the KOH treater 14 through conduit 18 under such extreme circumstances.

Temperature transducers 61, 62 and 63 are all located in different locations in the KOH treater 14. These transducers provide output signals 64-66 respectively which are each representative of the temperature in different parts of the KOH treater 14. Signals 64-66 are provided from the temperature transducers 61-63 as inputs to the averaging block 67.

The averaging block 67 provides an output signal 69 which is representative of the average temperature in the KOH bed treater 14. Signal 69 is provided as the process variable input to the temperature controller 71.

The temperature controller 71 is also provided with a set point signal 73 which is representative of the maximum desired average temperature in the KOH bed treater 14. Signal 73 will be chosen so as to catch a temperature runaway in the early states. A typical magnitude for signal 73 would be in the range of about 140° to about 160° F.

In response to signals 69 and 73, the temperature controller 72 provides an output signal 74 which is responsive to the difference between signals 69 and 73. Signal 74 is scaled so as to be representative of the position of the control valve 75, which is operably located in conduit 18, required to maintain the actual average in the KOH treater 14 substantially equal to the desired maximum temperature represented by signal 73. Signal 74 is provided as a control signal from the temperature controller 71 and the control valve 75 is manipulated in response thereto.

Signal 74 will typically have a magnitude such that the control valve 75 is fully closed. Only in those circumstances when a temperature runaway begins will signal 74 assume a magnitude which will enable the control valve 75 to become at least partially opened.

As was the case for signal 58 and as will be the case for control signals which will be described hereinafter, signal 74 may also be considered as being representative of a desired flow rate of fluid through conduit 18.

The pressure of the isobutane flowing through the standpipe 23 and also the isobutane in the external jacket 21 is controlled so as to insure that the isobutane will be vaporized (which insures maximum heat transfer) at a temperature which will still enable cooling water to condense the isobutane. This is accomplished by the pressure control described hereinafter.

Pressure transducer 81 in combination with a pressure sensing device, which is operably located in conduit 36, provides an output signal 82 which is representative of the actual pressure in the standpipe 23. Signal 82 is provided as the process variable input to the pressure controller 84.

The pressure controller 84 is also provided with a set point signal 85 which is representative of the desired pressure in the standpipe 23. This desired pressure will generally be in the range of about 70 to about 85 psig which will enable the isobutane to boil at a temperature in the range of about 110 to about 120° F.

In response to signals 82 and 85, the pressure controller 84 provides an output signal 87 which is responsive to the difference between signals 82 and 85. Signal 87 is scaled so as to be representative of the position of the control valve 88, which is operably located in conduit 36, required to maintain the actual pressure in the standpipe 23 substantially equal to the desired pressure represented by signal 85. Signal 87 is provided as a control signal from the pressure controller 84 and the control valve 88 is manipulated in response thereto.

In like manner, pressure transducer 91 in combination with a pressure sensing device, which is operably located in conduit 38, provides an output signal 92 which is representative of the actual pressure in the external jacket 21. Signal 92 is provided as the process variable input to the pressure controller 94.

The pressure controller 94 is also provided with a set point signal 95 which is representative of the desired pressure in the external jacket 21. Signal 95 will generally have a magnitude in the same range as signal 85 but the magnitude of signal 95 may be different than the magnitude of signal 85 since a larger volume of isobutane is contained in the external jacket 21.

In response to signals 92 and 95, the pressure controller 94 provides an output signal 96 which is responsive to the difference between signals 92 and 95. Signal 96 is scaled so as to be representative of the control valve 98, which is operably located in conduit 38, required to maintain the actual pressure in the external jacket 21 substantially equal to the desired pressure represented by signal 95. Signal 96 is provided as a control signal from the pressure controller 94 control valve 98 is manipulated in response thereto.

Liquid level control is also utilized for the external jacket 21. In particular, for a given volume of the external jacket 21, there will be some level of isobutane which will enable the isobutane to boil at the pressure represented by signal 95 and with the average amount of heat which is absorbed from the KOH treater 14 by the isobutane in the external jacket 21.

Level transducer 101 provides an output signal 102 which is representative of the actual liquid level in the external jacket 21. Signal 102 is provided as the process variable input to the level controller 103.

The level controller 103 is also provided with a set point signal 105 which is representative of the desired liquid level in the external jacket 21 as previously described.

In response to signals 102 and 105, the level controller 103 provides an output signal 106 which is responsive to the difference between signals 102 and 105. Signal 106 is scaled so as to be representative of the position of the control valve 108, which is operably located in conduit 37, required to maintain the actual liquid level in the external jacket 21 substantially equal to the desired liquid level represented by signal 105. Signal 106 is provided as a control signal from the level controller 103 and the control valve 108 is manipulated in response thereto.

Level control is also utilized for the overhead accumulator 48. It is also noted that makeup isobutane would generally be added to conduit 31.

Lever transducer 111 provides an output signal 112 which is representative of the actual liquid level in the accumulator 48. Signal 112 is provided as the process variable input to the level controller 114. The level controller 114 is also provided with a set point signal 116 which is representative of the desired liquid level in the accumulator 48.

In response to signals 112 and 116, the level controller 114 provides an output signal 117 which is responsive to the difference between signals 112 and 116. Signal 117 is scaled so as to be representative of the position of the control valve 118, which is operably located in conduit 31, required to maintain the actual liquid level in the accumulator 48 substantially equal to the desired liquid level represented by signal 116. Signal 117 is provided as a control signal from the level controller 117 and control valve 118 is manipulated in response thereto.

In summary, a desired operating pressure in the KOH treater is maintained by pressure controller 54. Heat exchange is utilized to prevent a temperature runaway in the KOH treater 14. The pressure of the isobutane is manipulated so as to allow boiling at a temperature at which the isobutane can still be condensed by cooling water. Also, the liquid level in the external jacket is manipulated so as to insure that vaporization will occur. Bypassing of feed around the KOH bed treater is utilized only under extreme circumstances where the described heat exchange is not adequate to prevent a temperature runaway.

The invention has been described in terms of a preferred embodiment as illustrated in FIG. 1. Specific components which can be used in the practice of the invention as illustrated in FIG. 1 such as pressure transducers 51, 81 and 91; pressure controllers 54, 84 and 94; temperature transducers 61, 62 and 63; the average in block 67, temperature controller 71; level transducers 101 and 111; level controllers 103 and 114; and control valves 59, 75, 88, 98, 108 and 118 are each well known, commercially available control components such as are described at length in Perry's Chemical Engineer's Handbook, 4th Edition, Chapter 22, McGraw Hill.

While the invention has been described in terms of the presently preferred embodiment, reasonable variations and modifications are possible by those skilled in the art. Such modifications and variations are within the scope of the described invention and the appended claims.

That which is claimed is:

1. Apparatus comprising:

a KOH treater;

means for providing propane containing HF acid as a feed to said KOH treater;

means for withdrawing propane containing a substantially reduced concentration of HF acid with respect to the concentration of HF acid in said feed provided to said KOH treater, from said KOH treater;

means for passing a cooling fluid in heat exchange with the external surface of said KOH treater, wherein said cooling fluid withdraws heat caused by the reaction of KOH and HF acid from said KOH treater and wherein said means for passing said cooling fluid in heat exchange with the external surface of said KOH treater comprises:

an external jacket surrounding said KOH treater;

means for passing said cooling fluid through said external jacket, wherein said cooling fluid passes in heat exchange with the external surface of said KOH treater;

means for establishing a first signal representative of the selected pressure in said external jacket;

means for establishing a second signal representative of the actual pressure in said external jacket;

means for comparing said first signal and said second signal and for establishing a third signal which is responsive to the difference between said first signal and said second signal and said third signal is scaled so as to be representative of the rate in which vapor should be withdrawn from said external jacket so as to maintain the actual pressure in said external jacket substantially equal to the selected pressure represented by said first signal;

means for manipulating the withdrawal of vapor from said external jacket in response to said third signal;

means for establishing a fourth signal representative of the actual liquid level in said external jacket;

means for establish a fifth signal representative of the selected liquid level in said external jacket;

means for comparing said fourth signal and said fifth signal and for establishing a sixth signal which is responsive to the difference between said fourth signal and said fifth signal, wherein said sixth signal is scaled so as to be representative of the rate at which liquid should be withdrawn from said external jacket in order to maintain the actual liquid level in said external jacket substantially equal to the selected liquid level represented by said fifth signal; and means for manipulating the withdrawal of liquid from said external jacket in response to said sixth signal.

2. Apparatus in accordance with claim 1 wherein said means for passing said cooling fluid in heat exchange with said KOH treater additionally comprises:

at least one standpipe passing through said KOH treater;

means for providing said cooling fluid to said at least one standpipe, wherein said at least one standpipe is not in fluid communication with the fluid in said external jacket;

means for establishing a seventh signal representative of the actual pressure in said at least one standpipe;

means for establishing an eighth signal representative of the selected pressure in said at least one standpipe;

means for comparing said seventh signal and said eighth signal and for establishing a ninth signal which is responsive to the difference between said seventh signal and said eighth signal, wherein said ninth signal is scaled so as to be representative of the rate at which fluid should be withdrawn from said at least one standpipe in order to maintain the actual pressure in said at least one standpipe substantially equal to the selected pressure represented by said eighth signal; and means for manipulating the rate at which fluid is withdrawn from said at least one standpipe in response to said ninth signal.

3. Apparatus in accordance with claim 2 wherein said cooling fluid is isobutane and wherein said apparatus additionally comprises:

a heat exchanger;

an accumulator;

means for providing cooling water to said heat exchanger;

means for combining the isobutane withdrawn from said external jacket and from said at least one standpipe and for passing the thus combined isobutane through said heat exchanger to said accumulator, wherein said isobutane is condensed in said heat exchanger;

means for withdrawing isobutane from said accumulator and for providing the thus withdrawn isobutane to said external jacket and said at least one standpipe;

means for establishing a tenth signal representative of the actual liquid level in said accumulator;

means for establishing an eleventh signal representative of the selected liquid level in said accumulator;

means for comparing said tenth signal and said eleventh signal and for establishing a twelfth signal which is responsive to the difference between said tenth signal and said eleventh signal, wherein said twelfth signal is scaled so as to be representative of the rate at which isobutane should be withdrawn from said accumulator in order to maintain the actual liquid line in said accumulator substantially equal to the selected liquid level represented by said eleventh signal; and means for manipulating the rate at which isobutane is withdrawn from said accumulator in response to said twelfth signal.

4. Apparatus in accordance with claim 1, additionally comprising:

means for bypassing at least a portion of the propane feed containing HF acid around said KOH treater;

means for establishing a first signal representative of the average temperature in said KOH treater;

means for establishing a second signal representative of the selected maximum average temperature in said KOH treater;

means for comparing said first signal and said second signal and for establishing a third signal which is responsive to the difference between said first signal and said second signal, wherein said third signal is scaled so as to be representative of the rate at which said propane containing HF acid should be bypassed around said KOH treater in order to prevent the average temperature in said KOH treater from exceeding the selected maximum average temperature represented by said second signal; and means for manipulating the bypassing of said propane containing HF acid around said KOH treater in response to said third signal.

5. Apparatus in accordance with claim 1 additionally comprising:

means for establishing a first signal representative of the actual pressure of the propane withdrawn from said KOH treater;

means for establishing a second signal representative of the selected pressure of the propane withdrawn from said KOH treater;

means for comparing said first signal and said second signal and for establishing a third signal which is responsive to the difference between said first signal and said second signal, wherein said third signal is scaled so as to be representative of the rate at which propane should be withdrawn from said KOH treater in order to maintain the actual pressure represented by said first signal substantially equal to the selected pressure represented by said second signal; and means for manipulating the rate at which propane is withdrawn from said KOH treater in response to said third signal.

* * * * *